United States Patent [19]

Bogeso et al.

[11] Patent Number: 4,873,344

[45] Date of Patent: Oct. 10, 1989

[54] CYANO CONTAINING INDENE DERIVATIVES

[75] Inventors: Klaus P. Bogeso, Molleaaparken; Michael B. Sommer, Markmandsgade, both of Denmark

[73] Assignee: H. Lundbeck A/S, Copenhagen-Valby, Denmark

[21] Appl. No.: 124,820

[22] Filed: Nov. 24, 1987

[30] Foreign Application Priority Data

Dec. 1, 1986 [GB] United Kingdom ............... 8628644

[51] Int. Cl.$^4$ ................ C07C 121/64; C07D 333/24
[52] U.S. Cl. ................................. 541/77; 546/173; 546/330; 548/560; 549/65; 549/74; 549/442
[58] Field of Search ............... 558/426; 549/65, 74, 549/77

[56] References Cited

U.S. PATENT DOCUMENTS 3,657,258 4/1972 Treiber et al. ............... 558/426 X

Primary Examiner—Joseph Paul Brust
Attorney, Agent, or Firm—Gordon W. Hueschen

[57] ABSTRACT

The present invention relates to novel indene derivatives with the general formula I:

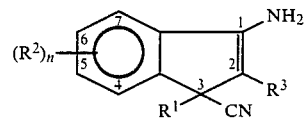

wherein $R^1$ is
(a) a phenyl group optionally substituted with one or two groups selected from halogen, lower alkyl, lower alkoxy, lower alkylthio, lower alkylsulfonyl, dilower alkylamino, acylamino such as acetylamino, cyano, trifluoromethyl, trifluoromethoxy, pyrrole and dilower alkylpyrrole,
(b) a polycyclic aromatic or heteroaromatic group, such as naphthalene or quinoline,
(c) a heteroaromatic group such as thiophene, pyridine, and pyrrole, optionally substituted with one or more groups selected from halogen, lower alkyl, lower alkoxy, lower alkylthio, trifluoromethyl or trifluoromethoxy, $R_2$ is selected from H, halogen, lower alkyl, benzyl, lower alkylthio, methoxy, lower alkylsulfonyl, dilower alkylsulfamoyl, acylamino such as acetylamino, benzylamino, dilower alkylamino, cyano, pyrrole, dilower alkylpyrrole, trifluoromethyl and trifluoromethoxy, $R^3$ is CN, COOR$^4$, —CON(R$^4$)$_2$ or COR$^4$, where R$^4$ is a lower alkyl group, and "n" is an integer of from 1–3 inclusive.

The indene derivatives of formula I are, when $R^1$ is as defined under (a) above, valuable intermediates which are useful in the preparation of pharmacologically effective indane and indene derivatives known from e.g. U.S. Pat. Nos. 4,443,448 and 4,525,360.

Moreover, the invention relates to a method for the preparation of the compounds of formula I and to a method for the preparation of compounds of the following formula IV:

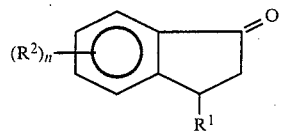

wherein $R^1$, $R^2$ and "n" are as defined above.

9 Claims, No Drawings

CYANO CONTAINING INDENE DERIVATIVES

BACKGROUND OF THE INVENTION

The compounds of formula IV, wherein $R^1$ is as defined under (a) above, are known from U.S. Pat. Nos. 4,443,448 and 4,525,360 and are themselves valuable intermediates for the preparation of pharmacologically active indanes and indenes known from the aforesaid U.S. patents.

The novel indenes of Formula I make it also possible to prepare the intermediates IV in excellent yield and with a variation in the substituent $R^1$ of a much wider scope than the method described in the abovementioned U.S. Patents.

SUMMARY OF THE INVENTION

According to the present invention it has surprisingly been found that 2-halogenobenzonitriles undergo extremely easy nucleophilic aromatic substitution of halogen with carbanions generated from aryl- and heteroarylacetonitriles thereby producing compounds of the general Formula II in the following scheme. The compounds of Formula II may either be isolated in excellent yields or further reacted in situ with halogenoacetic acid derivatives or with lower alkylhalogenomethyl ketones. The products thus formed undergo spontaneous cyclisation, thereby forming the compounds of formula I.

The sequence of reactions may be illustrated in the following reaction scheme:

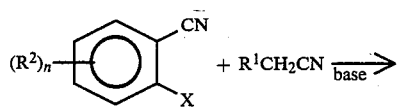

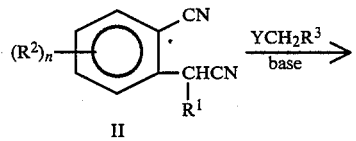

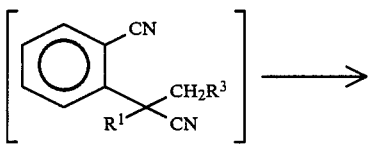

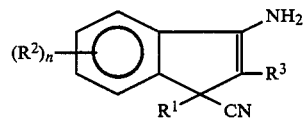

I wherein X is halogen, preferably F, Cl or Br, Y is Cl, Br or I, and $R^1$, $R^2$, $R^3$ and "n" are as defined above.

The compounds of formula I may alternatively be prepared by reacting 2-halogenobenzonitriles with 3-cyano-3-arylpropionic acid derivatives or with 3-cyano-3-heteroarylpropionic acid derivatives, with 4-(lower alkyl)-4-oxo-2-arylbutyronitriles or with 4-(lower alkyl)-4-oxo-2-heteroarylbutyronitriles according to the following reaction scheme:

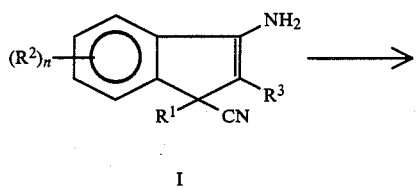

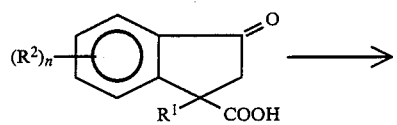

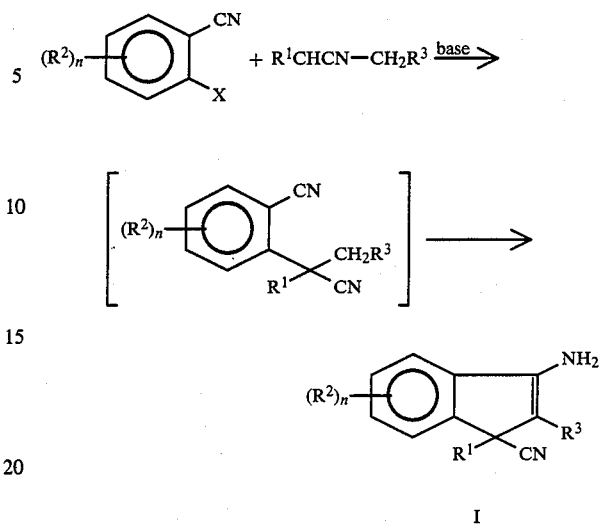

I

According to the present invention the compounds of formula I may easily be converted to the compounds of formula IV. The conversion may be illustrated by the following reaction scheme:

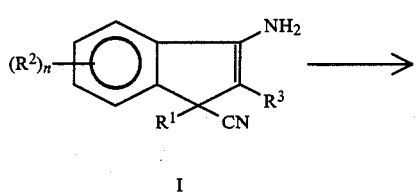

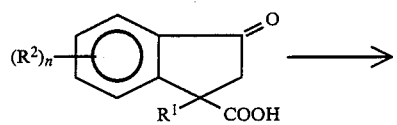

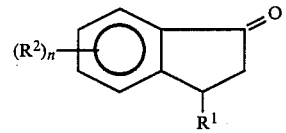

IV

The method of the invention comprises
(a) reacting a 2-halogenobenzonitrile of formula V:

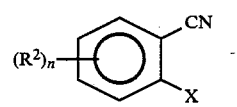

wherein $R^2$, X and "n" are as defined above, with a compound of the formula: $R^1CH_2CN$, wherein $R^1$ is as defined above, producing the compound with formula II:

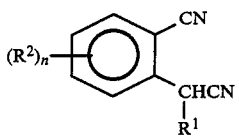

which may either be (1) isolated and further reacted in an organic solvent with a compound of formula: $YCH_2R^3$, wherein Y and $R^3$ are as defined above, thereby producing a compound of formula I, or (2) further reacted in situ with a compound of the formula: $YCH_2R^3$, thereby producing a compound of formula I, or (b) reacting a 2-halogenobenzonitrile of formula V with a compound of formula: $R^1$—CHCN—$CH_2R^3$, wherein $R^1$ and $R^2$ are as defined above;

whereupon the resulting compound of formula I is isolated.

The methods (a) and (b) are preferably carried out in an aprotic organic solvent such as N,N-dimethylformamide (DMF), dimethylsulfoxide (DMSO), N-methylpyrrolidone (NMP), 1,2-dimethoxyethane (DME), tetrahydrofuran (THF) or the like, under anhydrous conditions in an inert atmosphere, in the presence of an alkaline substance such as an alkalimetal alcoholate such as potassium tert-butoxide, sodium hydride, sodium amide or an alkalimetal carbonate such as potassium or cesium carbonate, at temperatures between 15° C. and 60° C.

The present invention further provides a method for the preparation of compounds of Formula VI, which comprises:

heating a compound of formula I

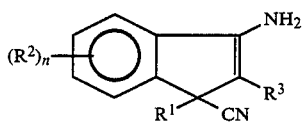

wherein $R^1$, $R^2$, $R^3$ and "n" are as defined above, under hydrolytic conditions, optionally under oxidative conditions, and isolating the compound of formula III:

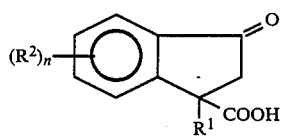

and heating the compound of formula III in a basic organic solvent, whereupon the indane of formula IV is isolated.

According to this method of preparation of indanes of formula III the compounds of formula I for which $R^3$ is CN, $COOR^4$ or $CON(R^4)_2$, wherein $R^4$ is as defined above, undergo hydrolysis and decarboxylation, preferably upon heating in mixtures of acetic acid, sulfuric acid and water, in mixtures of methanesulfonic acid and water or in mixtures of acetic acid and concentrated hydrochloric acid at temperatures between about 100° C. and 120° C., thereby forming the compounds of formula III. The compounds of formula I for which $R^3$ is $COR^4$, wherein $R^4$ is as defined above, undergo the oxidative Baeyer-Villiger rearrangement, known e.g. from Jerry March: "Advanced Organic Chemistry", 3.Ed., Wiley-Interscience New York 1985, upon treatment with peroxycarboxylic acids such as trifluoroperoxyacetic acid or meta-chloroperoxybenzoic acid (MCPBA) in inert organic solvents. The resulting compounds are subsequently hydrolysed and decarboxylated as described above for the compounds of formula I for which $R^3$ is CN, $COOR^4$ or $CON(R^4)_2$, thereby forming the compounds of formula III.

The subsequent conversion of the compounds of formula III into the indanes of formula IV is preferably carried out in weakly basic organic solvents such as pyridine, quinoline and N-methylpyrrolidone (NMP), optionally diluted with an inert organic solvent such as toluene, at temperatures between about 60° and 120° C.

The term "lower" in the foregoing and in the claims means from 1-6 carbon atoms inclusive, preferably from 1-4 carbon atoms inclusive.

In the novel indene derivatives of formula I, $R^1$ is preferably a phenyl group optionally substituted with one or two groups selected from chloro, fluoro, methyl, methoxy, acetylamino or trifluoromethyl, a pyrrole group optionally substituted with methyl or methoxy, a thiophene ring optionally substituted with methyl or fluoro, a pyridine ring optionally substituted with methyl or fluoro or a naphthyl ring; $R^2$ is H, Cl, Br, F, $CH_3$, $CH_3O$ or $CF_3$; $R^3$ is $COOCH_3$, —CN or —$CON(CH_3)_2$, and "n" is 1.

The methods of the invention shall in the following be illustrated by some examples which may not be construed as limiting.

EXAMPLE 1

1-Amino-3-cyano-3-(4-fluorophenyl)-6-nitro-1-inden-2-carboxylic acid methyl ester A suspension of 43.0 gr 3-cyano-3-(4-fluorophenyl)-propionic acid methylester, 40.0 gr 2-chloro-5-nitrobenzonitrile, 34.5 gr potassium carbonate and 7.5 gr tetrabutylammoniumhydrogen sulfate in 200 ml N,N-dimethylformamide (DMF) is stirred for 90 hrs at 50° C.

The mixture is cooled and poured into 200 ml toluene, 500 ml dilute hydrochloric acid are added gradually, and the mixture is stirred for 2 hrs at ambient temperature. The crystallized product is isolted by filtration and purified with cold toluene.

Yield: 46.0 gr (62% of the theoretical amount). Mp. (from ethanol): 286°–289° C.

Analysis: $C_{18}H_{12}FN_3O_4$ requires: %C: 61.18 %H: 3.43 %N: 11.90; found: %C: 60.72 %H: 3.21 %N: 11.66.

EXAMPLE 2

1-Amino-3-cyano-3-(4-fluorophenyl)-6-trifluoromethyl-1-inden-2-carboxylic acid methylester The following operations are performed under dry nitrogen. To a well-stirred suspension of 10.25 kg potassium tert-butoxide in 30 liters 1,2-dimethoxyethane (DME) is added gradually a solution of 6 kg 4-fluorobenzylcyanide and 9.6 kg 2-chloro-5-trifluoromethylbenzonitrile in 15 ltr DME, maintaining an internal temperature of approx. 20° C. The reaction mixture is subsequently stirred for one hour at ambient temperature. 9.7 kg methylchloroacetate is added gradually, and the mixture is stirred overnight at ambient temperature.

The following day the reaction mixture is heated to 60° C. and stirred for 3 hours. The reaction mixture is cooled and quenched with dilute acetic acid. The main part of the solvent (DME) is removed in vacuo, and subsequent work-up in the usual manner gives the product 1-amino-3-cyano-3-(4-fluorophenyl)-6-trifluoromethyl-1-inden-2-carboxylic acid methylester.

Yield: 13.84 kg (83% of the theoretical amount). Mp. (from ethanol): 178°–179° C.

Analysis: $C_{19}H_{12}F_4N_2O_2$ requires: %C: 60.64 %H: 3.22 %N: 7.45; found: %C: 60.50 %H: 3.19 %N: 7.37.

EXAMPLE 3

1-Amino-3-cyano-3-(4-fluorophenyl)-1-inden-2-carboxylic acid methyl ester

The following operations are performed under dry nitrogen.

To a stirred solution of 234.6 gr potassium tert.-butoxide in 800 ml N,N-dimethylformamide (DMF) is added gradually a solution of 135.1 gr 4-fluorobenzylcyanide and 144.5 gr 2-chlorobenzonitrile in 400 ml DMF, maintaining an internal temperature between 25° C. and 30° C. (ice bath). The reaction mixture is subsequently stirred for 1 hour at ambient temperature. 115 ml methylchloroacetate are added gradually, and the reaction mixture is stirred overnight at ambient temperature.

The following day the reactoion mixture is heated to 50° C. and stirred for 2 hrs., cooled and poured into a mixture of 3.5 ltr dilute hydrochloric acid, 500 ml n-heptane and 250 ml toluene. The product crystallizes within an hour and is isolated by filtration of the suspension. The crystalline product is purified with additional amounts of water (2×500 ml) toluene (2×100 ml) and n-heptane (2×250 ml). The product is dried in vacuo at 60° C. overnight.

Yield: 260.6 gr (84.5% of the theoretical amount). Mp. 198°–202° C.

Analysis: $C_{18}H_{13}FN_2O_2$ requires: %C: 70.11 %H: 4.26 %N: 9.09; found: %C: 69.80 %H: 4.17 %N: 8.83.

EXAMPLE 4

1-Amino-6-chloro-3-cyano-3-(thien-3-yl)-1-inden-2-carboxylic acid methyl ester

The following operations are performed under dry nitrogen.

To a stirred suspension of 18.9 gr potassium tert-butoxide in 75 ml anhydrous 1,2-dimethoxyethane (DME) is added gradually a solution of 15.0 gr 2,5-dichlorobenzonitrile and 10.0 gr thiophene-3-acetonitrile in 150 ml anhydrous DME, maintaining an internal temperature between 15° C. and 20° C. (ice bath). The reaction mixture is subsequently stirred for 15 minutes at 20° C. and cooled to 10° C. 25 ml methylchloroacetate are added gradually, and the reaction mixture is stirred overnight at ambient temperature.

The following day the reaction mixture is quenched with dilute hydrochloric acid. Extractive work-up with diethyl ether in the usual manner gives 20.0 gr crystalline product (74% of the theoretical amount).

Melting point (recryst. from ethanol): 199°–201° C.

Analysis: $C_{16}H_{11}ClN_2O_2S$ requires %C: 58.09 %H: 3.36 %N: 8.47; found %C: 57.71 %H: 3.16 %N: 8.20.

EXAMPLE 5

2-Cyano-4′-fluorobenzhydrylcyanide

The following operations are performed under dry nitrogen.

To a stirred solution of 700 gr potassium tert-butoxide in 3.6 ltr N,N-dimethylformamide (DMF) is added gradually a solution of 401.4 gr 4-fluorobenzylcyanide and 429.2 gr 2-chlorobenzonitrile in 1.2 ltr DMF, maintaining an internal temperature between 25° C. and 30° C. (ice bath). The reaction mixture is subsequently stirred for one hour at ambient temperature and quenched with dilute hydrochloric acid. Extractive work-up with diethylether gives the product 2-cyano-4′-fluorobenzhydrylcyanide.

Yield: 602.1 gr (85.8% of the theoretical amount). mp. 87°–89° C.

Yield: $C_{15}H_9FN_2$ requires: %C: 76.25 %H: 3.85 %N: 11.86; found: %C: 76.05 %H: 3.74 %N: 11.55.

EXAMPLE 6

1-Amino-2-acetyl-3-cyano-3-(4-fluorophenyl)-1-indene

The following operations are performed under dry nitrogen.

5.0 gr 2-cyano-4′-fluorobenzhydrylcyanide are added to a well-stirred suspension of 4.4 gr anhydrous potassium carbonate in 25 ml DMF. The reaction-mixture is stirred efficiently for 30 minutes, and 5.0 gr chloroacetone are added gradually with cooling. The resulting reaction-mixture is stirred for 48 hours at ambient temperature. Subsequent extractive work-up with diethyl ether gives the product 1-amino-2-acetyl-3-cyano-3-(4-fluorophenyl)-1-inden.

Yield: 4.9 gr (79% of the theoretical amount). Mp. 190°–192° C.

Analysis: $C_{18}H_{13}FN_2O$ requires: %C: 73.95 %H: 4.49 %N: 9.59; found: %C: 73.77 %H: 4.53 %N: 9.42.

EXAMPLE 7

3-carboxy-3-(4-fluorophenyl)-indan-1-one

A mixture of 50.0 gr 1-amino-3-cyano-3-(4-fluorophenyl)-1-inden-2-carboxylic acid methylester and 250 ml glacial acetic acid is heated to about 90° C. and stirred for about 15 minutes until a homogeneous solution is formed. A mixture of 80 ml concentrated sulfuric acid and 40 ml water is added gradually maintaining an internal temperature of 90°–100° C. The temperature is subsequently raised to 110° C., and the reaction-mixture is stirred at this temperature for 4 hours and poured into crushed ice. Extractive work-up with toluene gives the product 3-carboxy-3-(4-fluorophenyl)-indan-1-one.

Yield: 40.0 gr (91.0% of the theoretical amount). Mp. 106°–108° C.

Analysis: $C_{16}H_{11}FO_3$ requires: %C: 71.10 %H: 4.11; found: %C: 71.01 %H: 4.22.

EXAMPLE 8

3-(4-fluorophenyl)-indan-1-one

The following operations are performed under dry nitrogen. A solution of 40.0 gr 3-carboxy-3-(4-fluorophenyl)-indan-1-one in 50 ml N-methylpyrrolidone is heated to 100° C. and stirred for 2 hours at this temperature. The reaction-mixture is cooled and poured into 250 ml water. Subsequent extractive work-up with ethylacetate give the product 3-(4-fluorophenyl)-indan-1-one.

Yield: 28.5 gr (85.0% of the theoretical amount). Mp. 120°–121° C.

Analysis: $C_{15}H_{11}FO$ requires: %C: 79.62 %H: 4.91; found: %C: 79.43 %H: 5.05.

The compounds of Formula I, which have been prepared under conditions equivalent to those described in examples 1–4, and 6, are listed in the following scheme:

![Formula I structure]

(in the following scheme "n" is 1)

| R¹ | R² | R³ | MP(°C.) |
|---|---|---|---|
| 4-(Acetylamino)-phenyl | H | COOCH₃ | 278–80 |
| 3-Chloro-4-methoxyphenyl | H | COOCH₃ | 185–87 |
| 2-Chlorophenyl | 6-Cl | COOCH₃ | 247–48 |
| 3,4-Dichlorophenyl | H | COOCH₃ | 198–200 |
| 2,4-Difluorophenyl | 6-Cl | COOCH₃ | 195–97 |
| 2,4-Difluorophenyl | H | COOCH₃ | 214–16 |
| 3,4-Dimethoxyphenyl | H | COOCH₃ | 120–24 |
| 2-Fluorophenyl | H | COOCH₃ | 208–10 |
| 2-Fluorophenyl | 6-Cl | COOCH₃ | 171–75 |
| 3-Fluorophenyl | 6-Cl | COOCH₃ | 211–13 |
| 4-Fluorophenyl | 7-Cl | COOCH₃ | 167–68 |
| 4-Fluorophenyl | 6-Br | COOCH₃ | 177–80 |
| 4-Fluorophenyl | 6-Me₂NSO₂ | COOCH₃ | 222–27 |
| 4-Fluorophenyl | 7-F | COOCH₃ | 127–29 |
| 4-Fluorophenyl | H | COOCH₃ | 197–98 |
| 4-Fluorophenyl | 6-CF₃ | COOCH₃ | 178–79 |
| 4-Fluorophenyl | 5-CF₃ | COOCH₃ | 183–85 |
| 4-Fluorophenyl | 7-OCH₃ | COOCH₃ | 181–85 |
| 4-Fluorophenyl | 6-OCH₃ | COOCH₃ | 179–81 |
| 4-Fluorophenyl | 6-NO₂ | COOCH₃ | 286–89 |
| 4-Fluorophenyl | 6-Cl | COOCH₃ | 177–80 |
| 4-Fluorophenyl | 4-Cl | COOCH₃ | 208–10 |
| 4-Fluorophenyl | 5-Br | COOCH₃ | 152–55 |
| 4-Fluorophenyl | 6-CH₃SO₂ | CN | 180–82 |
| 4-Fluorophenyl | H | CN | 175–77 |
| 4-Fluorophenyl | 5-Cl | COOCH₃ | 236–39 |
| 4-Fluorophenyl | 6-CH₃S | CN | 249–51 |
| 4-Fluorophenyl | 6-CN | COOCH₃ | 239–41 |
| 4-Fluorophenyl | H | COCH₃ | 190–92 |
| 3-Methoxy-4-chlorophenyl | H | COOCH₃ | oil |
| 4-Methoxyphenyl | H | COOCH₃ | 142–44 |
| 3,4-(Methylen-dioxy)phenyl | H | COOCH₃ | 169–73 |
| 4-Methylphenyl | 6-Cl | COOCH₃ | 230–35 |
| 1-Methylpyrrol-2-yl | 6-Cl | COOCH₃ | 214–16 |
| 1-Methylpyrrol-2-yl | H | COOCH₃ | 210–13 |
| 3-Methylthiene-2-yl | H | COOCH₃ | 168–70 |
| 4-Methylthiophenyl | H | CN | 234–38 |
| 1-Naphtyl | H | COOCH₃ | 228–31 |
| Phenyl | H | COOCH₃ | 184–88 |
| Phenyl | 7-Cl | COOCH₃ | 156–58 |
| Phenyl | 6-Cl | COOCH₃ | 212–14 |
| Phenyl | H | CON(CH₃)₂ | 240–41 |
| 3-Pyridyl | H | COOCH₃ | 140–42 |
| 2-Thienyl | 6-Cl | COOCH₃ | 214–16 |
| 2-Thienyl | H | COOCH₃ | 154–58 |
| 3-Thienyl | 6-CF₃ | COOCH₃ | 204–07 |
| 3-Thienyl | 6-CH₃ | COOCH₃ | 182–85 |
| 3-Thienyl | 6-F | COOCH₃ | 182–84 |
| 3-Thienyl | 6-Cl | COOCH₃ | 199–201 |
| 3-Thienyl | H | COOCH₃ | 160–61 |
| 3-Thienyl | 6-CH₃O | COOCH₃ | 203–05 |
| 3-Trifluoromethylphenyl | H | COOCH₃ | 202–04 |
| 3-Trifluoromethylphenyl | 6-Cl | COOCH₃ | 205–07 |

What we claim is:

1. An indene derivative of the formula I:

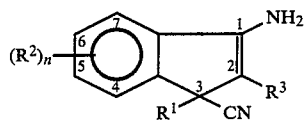

wherein R¹ is
(a) phenyl or phenyl substituted with one or two groups selected from halogen, lower alkyl, lower alkoxy, lower alkylthio, lower alkylsulfonyl, di-lower alkylamino, or carboxylic acid-derived acylamino, cyano, or trifluoromethyl, trifluoromethoxy,
(b) a bicyclic aromatic,
(c) a thiophene, or thiophene substituted with a substituent selected from halogen, lower alkyl, lower alkoxy, lower alkylthio, trifluoromethyl or trifluoromethoxy, and R² is selected from H, halogen, lower alkyl, benzyl, lower alkylthio, methoxy, lower alkylsulfonyl, dilower alkylsulfamoyl, carboxylic acid-derived acylamino, benzylamino, dilower alkylamino, cyano, trifluoromethyl and trifluoromethoxy, R³ is CN, COOR⁴, —CON(R⁴)₂ or COR⁴, where R⁴ is a lower alkyl group, and "n" is an integer of 1–3 inclusive.

2. An indene derivative according to claim 1, wherein R¹ is a phenyl or phenyl substituted with one or two groups selected from chloro, fluoro, methyl, methoxy, acetylamino and trifluoromethyl, thiophene or thiophene substituted with methyl, chloro or fluoro, or a naphthalene ring; R² is hydrogen, chloro, bromo, fluoro, methyl, methoxy or trifluromethyl; R³ is —COOCH₃, —CN or —CON(CH₃)₂, and "n" is 1.

3. An indene derivative according to claim 1, wherein R¹ is phenyl or phenyl substituted with chloro, fluoro or trifluoromethyl; R² is hydrogen, chloro, fluoro, methyl, methoxy or trifluoromethyl in the 6-position; R³ is —COOCH₃, —CN or —CON(CH₃)₂, and "n" is 1.

4. An indene derivative according to claim 1, wherein R¹ is thiophene or thiophene substituted with methyl or fluoro; R² is hydrogen, chloro, fluoro, methyl, methoxy or trifluoromethyl in the 6-position; R³ is —COOCH₃, —CN or —CON(CH₃)₂, and "n" is 1.

5. Compound of claim 1 being 1-Amino-3-cyano-3-(3,4-dichlorophenyl)-1-inden-2-carboxylic acid methyl ester.

6. Compound of claim 1 being 1-Amino-3-cyano-3-(4-fluorophenyl)-6-chloro-1-inden-2-carboxylic acid methyl ester.

7. Compound of claim 1 being 1-Amino-3-cyano-3-(4-fluorophenyl)-1-inden-2-carboxylic acid methyl ester.

8. Compound of claim 1 being 1-Amino-3-cyano-3-(thienyl-3)-6-chloro-1-inden-2-carboxylic acid methyl ester.

9. Compound of claim 1 being 1-Amino-3-cyano-3-(thienyl-3)-1-inden-2-carboxylic acid methyl ester.

* * * * *

UNITED STATES PATENT AND TRADEMARK OFFICE
CERTIFICATE OF CORRECTION

PATENT NO. : 4,873,344

DATED : Oct. 10, 1989

INVENTOR(S) : Klaus P. Bogeso, Michael B. Sommer

It is certified that error appears in the above—identified patent and that said Letters Patent is hereby corrected as shown below:

Column 6, Line 13; "Yield:" should read -- Analysis: --

Column 7, Line 44; "3-Methylthiene-" should read -- 3-Methylthien --

Column 8, Line 14; "cyano, or trifluoromethyl, trifluoromethoxy," should read -- cyano, trifluoromethyl, or trifluoromethoxy, --

Column 8, Line 16; "aromatic," should read -- aromatic, or --

Column 8, Line 35; "trifluromethyl" should read -- trifluoromethyl --

Signed and Sealed this

Eighteenth Day of September, 1990

Attest:

HARRY F. MANBECK, JR.

*Attesting Officer*  *Commissioner of Patents and Trademarks*